United States Patent [19]

Fleming

[11] Patent Number: 5,268,498
[45] Date of Patent: Dec. 7, 1993

[54] SYNTHESIS OF α-AMINONITRILES WITH RECYCLE OF AQUEOUS PHASE

[75] Inventor: Alison A. Fleming, Mohegan Lake, N.Y.

[73] Assignee: Akzo nv, Arnhem, Netherlands

[21] Appl. No.: 989,617

[22] Filed: Dec. 14, 1992

[51] Int. Cl.$^5$ .......................................... C07C 253/30
[52] U.S. Cl. ..................................................... 558/346
[58] Field of Search ........................................ 558/346

[56] References Cited

U.S. PATENT DOCUMENTS 2,164,781  7/1939  Platz et al. ...................... 562/507 X

OTHER PUBLICATIONS

Rappoport, "The Chemistry of the Cyano Group," (1970), pp. 74–75.
"The Merck Index" (1983), 10th Ed., p. ONR-87.
Hauser, et al.; J.A.C.S., 82 (1960), pp. 1786–1789.
Luten, Jr.; J. Org. Chem., 3 (1938–1939) pp. 588–597.
D. T. Mowry, "The Preparation of Nitriles", (1948), Chemical Reviews vol. 42, pp. 189, 238, 270–271, 279,281.
Y. M. Shatran et al., "Synthesis and Properties Of α-Aminonitriles", Russian Chemical Reviews 58(2) 148–162 (1989).

*Primary Examiner*—Joseph Paul Brust
*Attorney, Agent, or Firm*—Richard P. Fennelly; Louis A. Morris

[57] ABSTRACT

The bisulfite adduct of a carbonyl compound, amine, and alkali metal cyanide are reacted in aqueous media to form an organic layer containing the desired α-aminonitrile product and an aqueous layer containing alkali metal sulfite. The aqueous layer, after separation from the organic layer, can be used as the reaction medium in a fresh reaction of bisulfite adduct, amine and alkali metal cyanide after its pH has been adjusted to the moderately acidic range, e.g., a pH of about 4 to about 5.

7 Claims, No Drawings

SYNTHESIS OF α-AMINONITRILES WITH RECYCLE OF AQUEOUS PHASE

BACKGROUND OF THE INVENTION

The preparation of α-aminonitriles, which are recognized, for example, as intermediates for the synthesis of α-amino acids and nitrogen-containing heterocycles which are biologically important compounds, can be undertaken by reacting a carbonyl compound, such as an aldehyde or a ketone, for example, with amines and a cyanide source. One cyanide source which can be used is hydrogen cyanide. If hydrogen cyanide is not selected as the cyanide source, the carbonyl compound needs to be first reacted with one equivalent of bisulfite, such as sodium bisulfite, prior to adding the amine and cyanide source, such as alkali metal cyanide, to avoid imine formation. The amount of imine formation is also dependent upon the carbonyl compound used with, for example, a longer chain aldehyde, such as 2-ethylhexanal, yielding more imine formation than a shorter chain aldehyde, such as isobutyraldehyde. The reaction of a bisulfite adduct of the selected carbonyl compound, amine, and alkali metal cyanide in aqueous solution is the well-known Knoevenagel-Bucherer method (see Russian Chemical Reviews 58(2), 148-162 (1989); Chemical Reviews 42: 189 and following, at 238 (1942); and The Chemistry of the Cyano Group, Z. Rappoport, ed., p. 75 (1970).

Certain prior art references provide details of such synthetic procedures in which the desired α-aminonitrile is formed as an organic phase which separates from the aqueous layer which contains aqueous alkali metal sulfite. For example, in U.S. Pat. No. 2,164,781 the α-aminonitrile product in the Oil is indicated as being saponified in the reaction mixture by the addition of caustic. Hauser et al. in Journal of the American Chemical Society, Vol. 82, 1786-1789 (1960) indicates in its experimental section that the aqueous layer is extracted with ether, the ether extract is combined with the original organic layer, and the combination is dried. Presumably, the aqueous layer was discarded. Luten, Jr. et al., in Journal of Organic Chemistry, Vol. 3, 588-597 (1938-39) the α-aminonitrile layer is merely separated from the aqueous layer, is dried, and is vacuum distilled. Again, the aqueous layer is presumably discarded.

DESCRIPTION OF THE INVENTION

The present invention relates to an improved Knoevenagel-Bucherer method in which: (a) a bisulfite adduct of a carbonyl compound is reacted in aqueous solution with amine and alkali metal cyanide to form an organic layer containing the desired α-aminonitrile product and an aqueous layer containing an alkali metal sulfite; and (b) the aqueous layer containing the alkali metal sulfite is separated from the organic layer and used for fresh reaction of bisulfite adduct of the carbonyl compound, amine and alkali metal cyanide after having its pH adjusted to a moderately acidic pH.

The bisulfite reagent which is used to form the adduct previously mentioned can be an alkali metal bisulfite, such as sodium bisulfite, or can be another reagent which is capable of forming a bisulfite adduct with a carbonyl compound, such as sodium metabisulfite, also known as sodium pyrosulfite.

The carbonyl compound which is reacted with the bisulfite reagent in forming the adduct are those carbonyl compounds which are not derivatives of carboxylic acids but which, rather, have one or more hydrocarbyl groups directly bonded to the carbonyl radical, $C=O$. Both ketones ($R-C(O)R^1$) and aldehydes ($R-C(O)H$) are intended to be covered with R and $R^1$ being the same or different and selected from alkyl, aryl, alkylaryl, arylalkyl, and the like. Polyhydroxy substituted carbohydrate materials, such as aldoses and ketones are also intended to be covered. The aldehyde or ketone may contain either a straight chain or branched structure of from one to fourteen carbon atoms.

The amine which is reacted with the adduct previously described can be a primary or secondary amine containing one or more suitable hydrocarbyl groups, as appropriate, which can be selected from alkyl, aryl, alkaryl or aralkyl, for example. If desired, the amine can be an alkyl alkylene diamine of the formula $RNHR_1NH_2$ where R is alkyl, e.g., fatty alkyl of $C_{12}$ to $C_{22}$ alkyl and $R_1$ is alkylene.

The cyanide source used is an alkali metal cyanide such as sodium cyanide or potassium cyanide.

As would be appreciated by the person of ordinary skill in the art, the reaction is conducted in a solvent medium containing water, optionally with an organic co-solvent such as a water miscible solvent (e.g., an alcohol, tetrahydrofuran or dimethylsulfoxide) or a water immiscible solvent, such as methylene chloride or toluene, at temperatures of about 0° C. to the reflux temperature of the solvent, preferably 20° C. to 60° C.

The resulting reaction just described will yield an organic layer containing the desired α-aminonitrile product and an aqueous layer containing alkali metal sulfite as a byproduct. This invention relates to recycle and reuse of this aqueous layer in a fresh reaction of bisulfite adduct, amine and alkali metal cyanide.

The present invention is further illustrated by the Examples which follow.

EXAMPLES 1-6

These Examples illustrate the synthesis of aminonitrile derivatives of certain fatty amines and illustrates the effect on imine formation with variation of the equivalents of sodium bisulfite in the reaction medium.

The general procedure that was employed first dissolved the selected aldehyde and sodium bisulfite in a 4:1 (w/w) mixture of water and isopropyl alcohol at room temperature. The resulting mixture was then stirred at room temperature for one to two hours to insure bisulfite adduct formation. The selected amine was then added followed immediately by sodium cyanide. Stirring was continued at room temperature. The product separated out as a liquid from the aqueous layer, was washed with water, and then dried.

The Table set forth below shows the yields and product distributions (the latter being determined by quantitative $^{13}C$ NMR) as the relative amount of sodium bisulfite was varied:

| Aldehyde | Equivalents of NaHSO₃ | Yield | Product Distribution |
|---|---|---|---|
| Isobutyraldehyde | 1.00 | 94% | 97% aminonitrile<br>3% amine<br>0% imine |
| Isobutyraldehyde | 0.75 | 96% | 84% aminonitrile<br>8.5% imine<br>7.5% amine |
| Isobutyraldehyde | 0.50 | 95% | 90% aminonitrile<br>5% imine<br>5% amine |

-continued

| Aldehyde | Equivalents of NaHSO$_3$ | Yield | Product Distribution | |
|---|---|---|---|---|
| Isobutyraldehyde | 0.25 | 90% | 80% | aminonitrile |
| | | | 11% | imine |
| | | | 9% | amine |
| Isobutyraldehyde | 0.00 | 86% | 78.5% | aminonitrile |
| | | | 18% | imine |
| | | | 3.5% | amine |
| 2-ethylhexanal | 0.00 | 87% | 51.4% | aminonitrile |
| | | | 44.9% | imine |
| | | | 3.7% | amine |

EXAMPLES 7-11

In these Examples, 2-ethylhexanal was first treated with aqueous sodium bisulfite (pH=4 to 5) and then tetradecylamine and sodium cyanide were added to yield an α-aminonitrile product (in the organic layer) and sodium sulfite in an aqueous layer. The pH of the aqueous layer was about 11. Removal of the organic layer containing the desired α-aminonitrile product with its recovery produced a yield of α-aminonitrile of 93% with only 7% unreacted amine.

The above reaction was repeated three separate times with removal of the α-aminonitrile product, adjustment of the pH of the aqueous layer to 4-5, addition of fresh 2-ethylhexanal to the aqueous layer, followed by fresh addition of tetradecylamine and sodium cyanide. The resulting yields and product distributions from this recycle use of the sulfite anion were: (1) 83% yield with 90% α-aminonitrile; 8% amine; and 2% imine; (2) 83% yield with 93% α-aminonitrile and 7% amine; and (3) 93% yield with over 95% α-aminonitrile and no amine or imine formation.

Repeating the first described reaction with removal of the α-aminonitrile product, addition of fresh 2-ethylhexanal to the aqueous layer, no adjustment of the pH of the aqueous layer to 4-5, followed by fresh addition of tetradecylamine and sodium cyanide gave a 91% yield of a mixture with the following product distribution: over 90% imine and only 5-10% α-aminonitrile.

These Examples illustrate that the aqueous layer containing the sulfite anion can be reused for new reactions but such reuse necessitates pH adjustment from the basic conditions prevailing in the aqueous layer at the end of a reaction to an acidic pH range (e.g., 4-5).

The foregoing Examples have been presented for illustrative purposes only and, as such, should not be construed in a limiting sense. The scope of protection sought is set forth in the claims which follow.

I claim:

1. A process for forming α-aminotriles which comprises:
   (a) reacting a bisulfate adduct of a carbonyl compound, selected from the group consisting of an aldehyde and a ketone, with amine, selected from the group consisting of a primary amine and a secondary amine, and alkali metal cyanide, in an aqueous reaction medium, to form an organic layer containing the α-aminonitrile and an aqueous layer containing alkali metal sulfite; and
   (b) separating the aqueous layer containing the alkali metal sulfite from the organic layer for use in the fresh reaction of bisulfite adduct of the carbonyl compound, amine and alkali metal cyanide after the pH of the aqueous layer has been adjusted to a moderately acidic pH.

2. A process as claimed in claim 1 wherein the moderately acidic pH is from about 4 to about 5.

3. A process as claimed in claim 1 wherein the alkali metal is selected from the group consisting of sodium and potassium.

4. A process as claimed in claim 2 wherein the alkali metal is selected from the group consisting of sodium and potassium.

5. A process as claimed in claim 1 wherein the bisulfite adduct is derived from use of sodium bisulfite.

6. A process as claimed in claim 2 wherein the bisulfite adduct is derived from use of sodium bisulfite.

7. A process as claimed in claim 3 wherein the bisulfite adduct is derived from use of sodium bisulfite.

* * * * *